(12) United States Patent
de Beus et al.

(10) Patent No.: US 8,645,153 B2
(45) Date of Patent: Feb. 4, 2014

(54) SYSTEM AND METHOD FOR ENABLING A PROPER DISPENSATION OF MEDICATION

(75) Inventors: Eric A. de Beus, Redondo Beach, CA (US); Roman D. Liccini, Los Angeles, CA (US)

(73) Assignee: Xerox Corporation, Norwalk, CT (US)

( * ) Notice: Subject to any disclaimer, the term of this patent is extended or adjusted under 35 U.S.C. 154(b) by 2765 days.

(21) Appl. No.: 11/250,029

(22) Filed: Oct. 13, 2005

(65) Prior Publication Data

US 2007/0088576 A1  Apr. 19, 2007

(51) Int. Cl.
  *G06Q 10/00*  (2012.01)
(52) U.S. Cl.
  USPC .................................................. 705/2; 705/3
(58) Field of Classification Search
  USPC .......................................... 705/2–3; 600/300
  See application file for complete search history.

(56) References Cited

U.S. PATENT DOCUMENTS

| | | | | |
|---|---|---|---|---|
| 4,857,716 A | * | 8/1989 | Gombrich et al. | 235/375 |
| 5,393,100 A | | 2/1995 | Coe | |
| 5,883,370 A | * | 3/1999 | Walker et al. | 235/375 |
| 5,905,652 A | | 5/1999 | Kutsuma | |
| 5,995,938 A | * | 11/1999 | Whaley | 705/3 |
| 6,681,935 B1 | | 1/2004 | Lewis | |
| 7,201,275 B2 | * | 4/2007 | Nakagawa et al. | 206/531 |

* cited by examiner

*Primary Examiner* — Robert Morgan
*Assistant Examiner* — Rajiv Raj
(74) *Attorney, Agent, or Firm* — Michael J. Nickerson; Basch & Nickerson LLP

(57) ABSTRACT

A system and method of composing medicine orders is disclosed. Patient dosage information for multiple medications is merged into a personalized medication schedule for the consumer. The schedule is printed on paper divided into sections by lines of perforation. Individual doses of medication are added to each section corresponding to the instructions printed therein.

14 Claims, 3 Drawing Sheets

SYSTEM AND METHOD FOR ENABLING A PROPER DISPENSATION OF MEDICATION

BACKGROUND

Users of prescription medicines often have to take multiple medicines each day. In some cases, different doses of different medicines have to be taken at specified times of day. Patients, who suffer from other conditions requiring multiple medications, typically spend time each day selecting the pills to be taken that day, and placing the selected pills in a container with multiple compartments. This helps them remember when to consume the pills from the various compartments during the day.

Further difficulties that many patients face are that their ailments may often cause fatigue or depression and thus reduce their ability to accurately select the proper medicines for their daily medication regimen. Selecting and sorting multiple medications can also be a significant inconvenience for patients who experience painful movement such as those that suffer from arthritis of the digits, wrist, elbow or shoulder.

Health care providers such as nurses or other practitioners who do not prescribe, but who are responsible for administering medicine, are also challenged to accurately sort and select daily medicine for their patients. This is especially true in a hospital setting where nurses are often under significant stress. Such health care providers could benefit when multiple medicines for their patients are packaged with the proper doses for each time slot on their patients' schedule already selected and separated.

Furthermore, it is conventional for a doctor to prescribe one or more medications for a patient to take one or more times during the day, and perhaps at certain times of the day. The medications are usually in the form of pills, but may also be powders and liquids.

Particularly for the elderly, often more than one medication must be taken on a daily basis. Conventionally, various devices have been provided to make it easier for patients, in particular, elderly patients, to organize their daily medication. One of these devices is in the form of a container having different compartments, one compartment representing a different medication time. Such a conventional device does not necessarily provide any indication on when the tablets contained in a particular compartment must be taken. If the compartments are demarcated by a day designation and multiple tablets must be taken at different times during the day, the presence of several of the same tablet in the compartment does not give the elderly patient any information other than that all of those tablets must be taken during that particular day.

Another conventional solution is to provide a medicine scheduler which can be filled out by a doctor and provided to a patient with a graphic indication of the appearance of each tablet or medicine which must be taken, and specific instructions concerning each medication. This conventional solution still requires the patient to spend time each day selecting the pills that are associated with the scheduler, requiring the patient to have functional eyesight and the ability to discern between medications, to be taken that day.

A further conventional solution provides for the preparing of a document based on prescription information from a doctor and other information about the medicine and a medicine bag with such information printed thereon. As with the other conventional solutions, this conventional solution still requires the patient to manage multiple bags to ensure that the proper medication is taken and at the correct time.

Therefore, it is desirable to provide a method or system whereby the burden of selecting and sorting medications is shifted from the patients and other health care providers. Such a system would deliver medicine to those who administer or self-administer it packaged with the proper doses for each time slot on the schedule already selected and separated.

BRIEF DESCRIPTION OF THE DRAWING

The drawings are only for purposes of illustrating an embodiment and are not to be construed as limiting, wherein.

DETAILED DESCRIPTION

Figure 1:
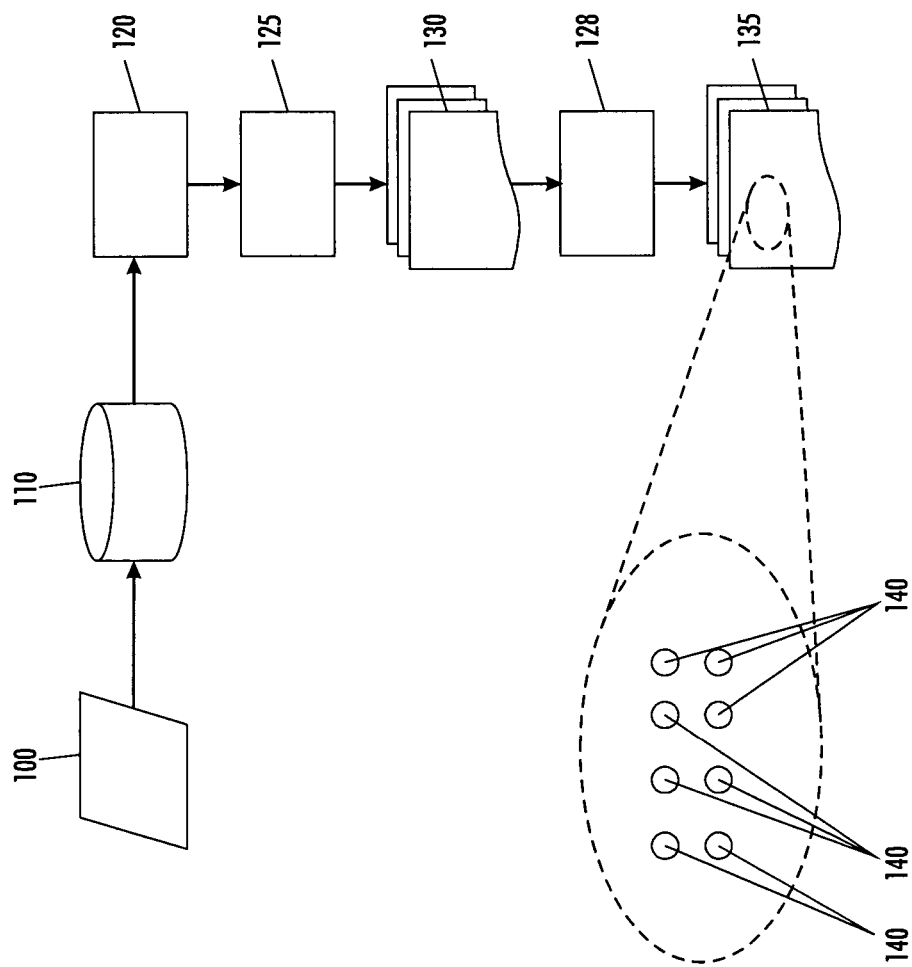
FIG. 1 is a block diagram illustrating an example of the method for enabling a proper dispensation of medication.

For a general understanding, reference is made to the drawings. In the drawings, like references have been used throughout to designate identical or equivalent elements. It is also noted that the drawings may not have been drawn to scale and that certain regions may have been purposely drawn disproportionately so that the features and concepts could be properly illustrated.

It is noted that although the various examples below refer to a prescription medication, the concepts thereof may also be readily applicable to the dispensing of over-the-counter medications.

FIG. 1 illustrates an example of enabling the proper dispensation of medication. Medication dosage information 100 is added to a computerized database 110. It is noted that this information may be added directly by a medical doctor authorized to write prescriptions or it may be added directly by a pharmacist taking the information from a doctor's written prescription.

The information from the database is retrieved by a processor 120 and used to generate a personalized schedule 130 for taking medication for a particular consumer to be printed by a printer 125. Since a consumer may have more than one prescription to be taken concurrently, the personalized schedule merges the dosages and dosage intervals to create a composite schedule for the consumer including all the concurrent prescriptions.

The personalized schedule 130 is printed by printer 125 on a recording medium, such as paper, that is divided into sections by perforations. It is noted that each section of the recording medium may contain printed instructions for one dose of a particular medication.

The print layout of the instructions can be organized so that a particular day's worth of medication may be all in one row of sections. Other organizational schemes may be utilized depending on the particulars of the personalized schedule 130, the layout of the sections, and the number of sections on the recording medium. It is noted that either the layout or arrangement of the sections on the recording medium may be varied; therefore printing the personalized schedule 130 requires entering the type of layout for a corresponding recording medium that is being loaded into the printer. This may be similar to what is conventionally done when printing labels; i.e., the label type is entered and the processor automatically arranges the print information to correspond to the label layout on the recording medium.

One example of a personalized schedule is for the consumer to take medication "A" everyday at 9:00 AM and medication "B" everyday at 7:30 PM. In this example, the layout of the instructions can be configured to the particular layout of the recording medium.

For example, if the recording medium had fourteen columns of sections, each row of sections may correspond to a week instead of a day. Thus, the personalized schedule 130 printed on the recording medium would have a heading over the first two columns labeled "Monday," and the two sections corresponding to the first two columns and the first row would have printed therein information, "A . . . 9:00 AM . . . " and "B . . . 7:30 PM . . . " respectively, representing the identification of the medication, time to take medication and any other information related to properly taking the medication.

In another example, if the recording medium had seven columns of sections, each row of sections may correspond to a medication type. Thus, the personalized schedule 130 printed on the recording medium would have a heading over the first column labeled "Monday," a heading for the first row labeled "A," and a heading for the second row labeled "B." The two sections corresponding to the first two rows and the first column would have printed therein information, "A . . . 9:00 AM . . . " and "B . . . 7:30 PM . . . " respectively, representing the identification of the medication, time to take medication and any other information related to properly taking the medication.

In a third example, if the recording medium had seven rows of sections, each row of sections may correspond to a day in the week. Thus, the personalized schedule 130 printed on the recording medium would have a heading over the first row labeled "Monday," a heading for the second row labeled "Tuesday," and a heading for the third row labeled "Wednesday," etc. In this example, the columns could represent time for taking medication; i.e., the first column could be labeled 9:00 AM. The first section corresponding to the first two rows and the first column would have printed therein information, "A . . . 9:00 AM . . . " and "A . . . 9:00 AM . . . " respectively, representing the identification of the medication, time to take medication and any other information related to properly taking the medication.

Thus, the recording medium can be laid out in a multitude of arrangements of sections. Knowing the layout of the recording medium, the processor. 120 arranges the medication information, using conventional techniques to optimize the medication information on the recording medium. It is noted that the processor 125 may allow the user to select the format of the personalized schedule 130 to correspond to a format that is more familiar to the user/consumer. In this example, the user overrides the optimized format and chooses a format that may be less confusing to the consumer.

After the recording medium is printed with the proper information, individual doses of medication 140 corresponding to the proper individual sections can be added to the sections using a medication device 128 to create a fully medication featured recording medium 135, which provides an information vehicle and carrier for the medication 140. The medication device 128 may affix a medication dose 140 in a blister style encasement to the section using a conventional adhesive. The encasement, recording medium, marking material, and adhesive may be digestible so that the consumer ingests the entire section.

On the other hand, the medication device 128 may impregnate the proper sections with the appropriate medication 140. In this example, the recording medium and marking material are both digestible.

Figure 2:
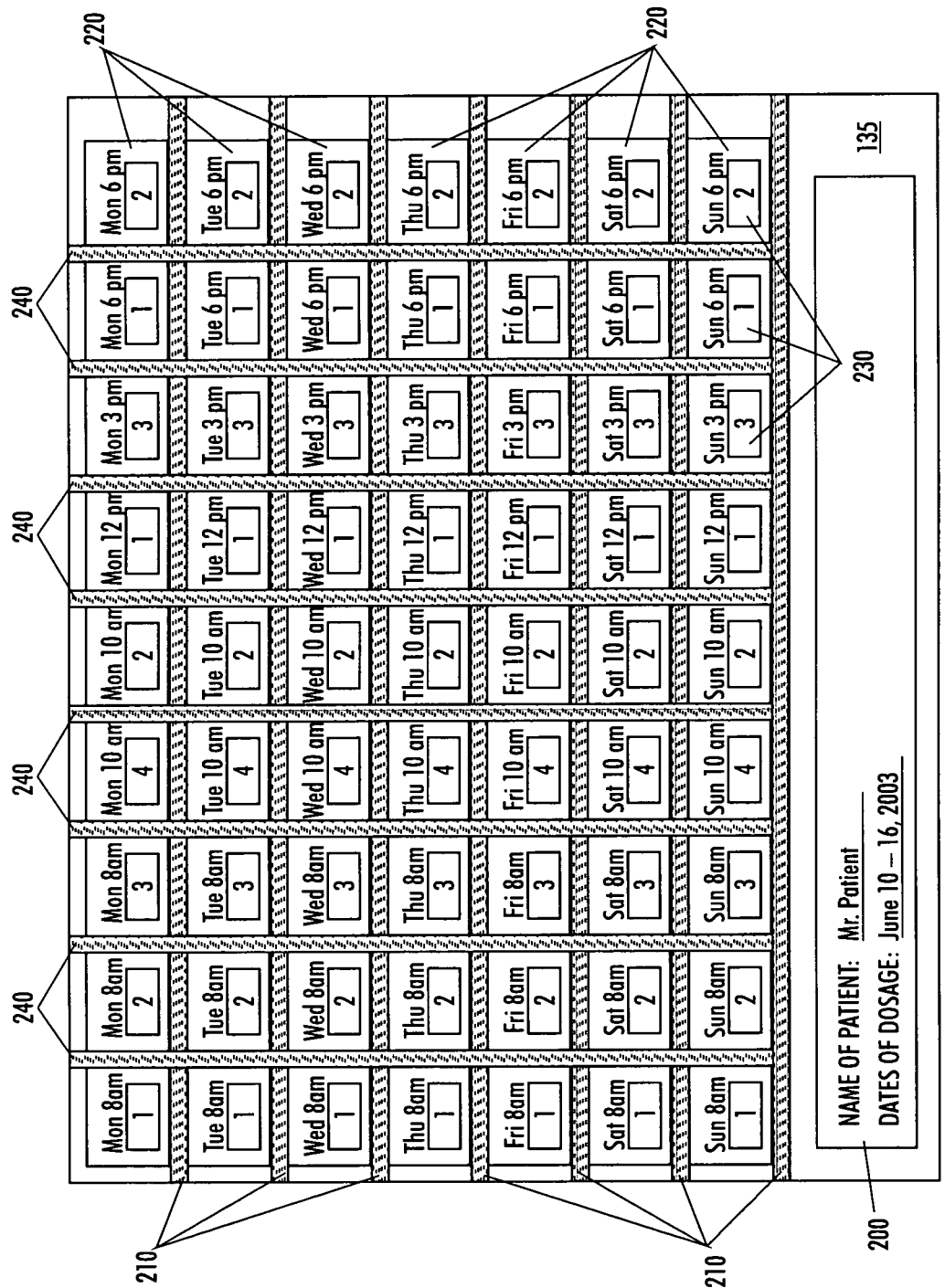
FIG. 2 is an illustration of an example of sectioned paper for adding medication thereto.

FIG. 2 illustrates an example of a sheet of the fully medication featured recording medium 135 with a recorded personalized schedule to be utilized in providing an information vehicle and carrier for the medication. An area 200 of the fully medication featured recording medium 135 is used to display patient information so as to guard against accidental misdirection of the personalized schedule 130 to the wrong patient.

In the illustrated example, each section 220 of the fully medication featured recording medium 135 is separable from the fully medication featured recording medium 135 as a unit by virtue of the horizontal perforations 210 and the vertical perforations 240. The horizontal perforations 210 and the vertical perforations 240 enable the patient or the one administering medication to remove and use individual doses of medication.

Each individual section 220 of the fully medication featured recording medium 135 contains printed information instructing which day and what time to take the dose of medication corresponding to the section. Within the section, a name or symbol of the medication 230 may also be printed.

It is noted that the sheet of the fully medication featured recording medium 135 may also include punch holes or other such device (not shown) to allow the sheet of the fully medication featured recording medium 135 to be bound in a booklet or binder.

Figure 3:
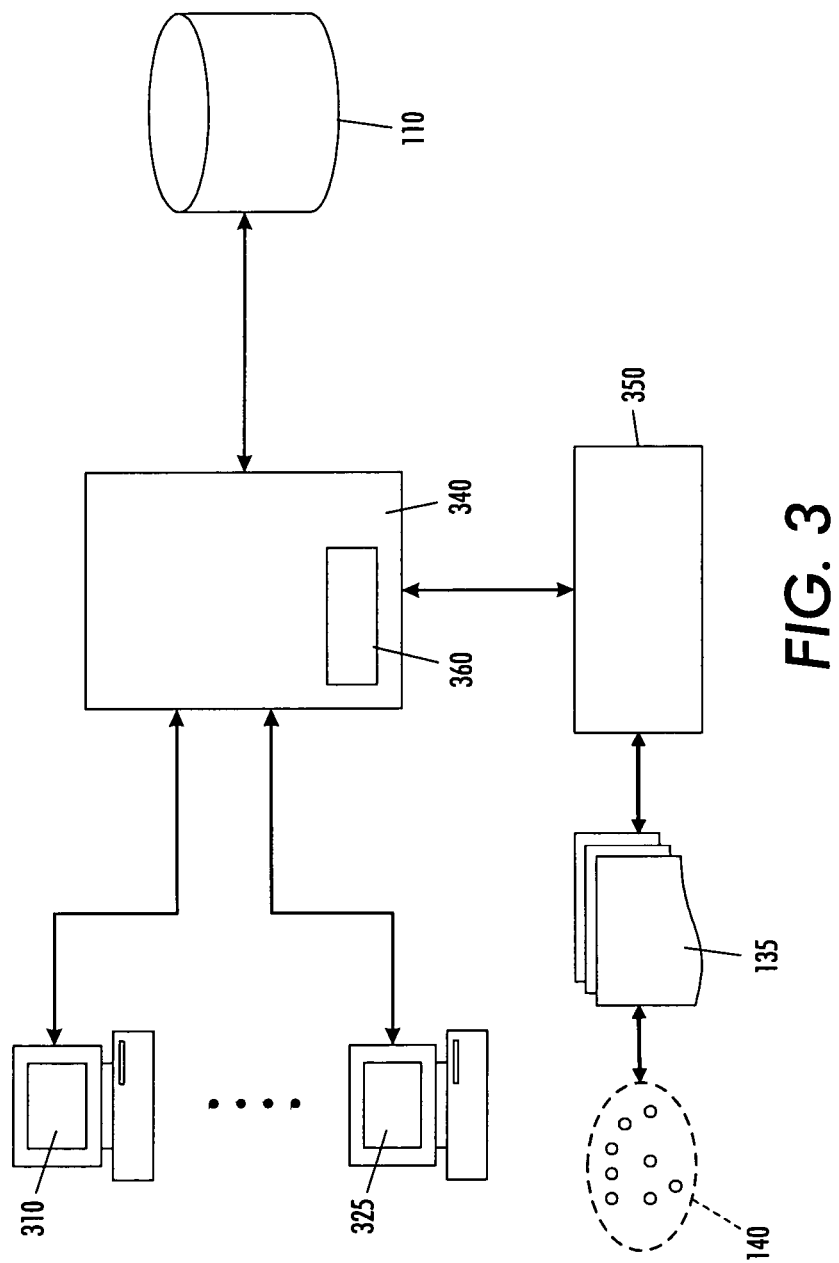
FIG. 3 is a block diagram depicting a possible configuration for the system for enabling a proper dispensation of medication.

FIG. 3 illustrates a web-based implementation of enabling the proper dispensation of medication. As illustrated in FIG. 3, a computer 310, operatively connected to a local or remote server 340, may be utilized by medical personnel to enter prescription information into a database 110 located on the server. Alternatively, a computer 325, operatively connected to the server 340, may be utilized by pharmacist personnel to enter doctor written prescription information into the database 110.

A medical dispensing and printing device 350, operatively connected to the server 340, receives personalized medication schedule information generated by the server 340. The medical dispensing and printing device 350, utilizing the received personalized medication schedule information, generates fully medication featured recording medium 135, which has printed thereon a personalized schedule. As in the previous examples, the fully medication featured recording medium 135 includes individual sections, separable by perforations. Individual doses of medication 140 are added to the individual sections in accordance with the dosage information printed in the individual sections.

It is noted that the medical dispensing and printing device 350 may be under the control of a pharmaceutical manufacturer, a pharmaceutical distributor, or a pharmacist.

In it noted that strict authentication and authorization control may be required to safeguard the information on patient medication from theft or tampering. Also, it may be imperative that only authorized medical doctors and authorized pharmacists have access to a system that could be used to dispense medications. To accomplish these goals, a security agent 360 can be embedded in the server 340 to provide authentication and authorization control.

In summary, a method for enabling a proper dispensation of medication generates a personalized schedule and dosage information for taking medication; prints the personalized schedule for taking medication on a recording medium, the recording medium being divided into sections by perforations, each section including printed instructions therein, said instructions corresponding to the medication associated with the section; and adds an appropriate amount of appropriate medication to each section, the appropriate amount of appropriate medication corresponding to the instructions printed therein.

The method for enabling a proper dispensation of medication may also receive, from a remote terminal, a dosage information for taking medication; generate a personalized schedule for taking the medication associated with the received dosage information; print the personalized schedule for taking medication on a recording medium, the recording medium being divided into sections by perforations, each section including printed instructions therein, said instructions corresponding to the medication associated with the section; and add an appropriate amount of appropriate medication to each section, the appropriate amount of appropriate medication corresponding to the instructions printed therein.

The recording medium may be digestible and an appropriate section of the recording medium is impregnated with the appropriate amount of appropriate medication. Also, an appropriate section of the recording medium may include a blister style encasement of the appropriate amount of appropriate medication or the recording medium is digestible and an appropriate section of the recording medium includes a digestible blister style encasement of the appropriate amount of appropriate medication.

Each section may be printed with medication identification information and/or medication chronological information. Each recording medium may contain sections associated with a pre-determined period of time and/or a pre-determined medication.

The method may also bind the recording medium in a booklet and the booklet may represent a pre-determined period of time.

It will be appreciated that various of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A method for enabling a proper dispensation of medication, comprising:
    generating a personalized schedule, the personalized schedule including time periods for taking medication, and dosage information for taking medication;
    printing, using a printing device, the personalized schedule for taking medication on a recording medium, the recording medium being divided into medication sections by perforations, each medication section including a portion of the printed personalized schedule therein, the portion of the printed personalized schedule corresponding to the medication associated with the medication section, the portion of the printed personalized schedule including an indication of a time of day to take the medication associated with the medication section, the recording medium being digestible; and
    adding an appropriate amount of appropriate medication to each medication section, the appropriate amount of appropriate medication corresponding to the dosage information for taking medication.

2. The method as claimed in claim 1, wherein an appropriate medication section of the recording medium is impregnated with the appropriate amount of appropriate medication.

3. The method as claimed in claim 1, wherein an appropriate medication section of the recording medium includes a blister style encasement of the appropriate amount of appropriate medication.

4. The method as claimed in claim 1, wherein an appropriate medication section of the recording medium includes a digestible blister style encasement of the appropriate amount of appropriate medication.

5. The method as claimed in claim 1, wherein each medication section is printed with medication identification information.

6. The method as claimed in claim 1, further comprising:
    binding the recording medium in a booklet.

7. The method as claimed in claim 6, wherein the booklet represents a pre-determined period of time.

8. A method for enabling a proper dispensation of medication, comprising:
    receiving, from a remote terminal, a dosage information for taking medication;
    generating a personalized schedule, the personalized schedule including time periods for taking medication, and dosage information for taking medication;
    printing, using a printing device, the personalized schedule for taking medication on a recording medium, the recording medium being divided into medication sections by perforations, each medication section including a portion of the printed personalized schedule therein, the portion of the printed personalized schedule corresponding to the medication associated with the medication section, the portion of the printed personalized schedule including an indication of a time of day to take the medication associated with the medication section, the recording medium being digestible; and
    adding an appropriate amount of appropriate medication to each medication section, the appropriate amount of appropriate medication corresponding to the dosage information for taking medication.

9. The method as claimed in claim 8, wherein an appropriate medication section of the recording medium is impregnated with the appropriate amount of appropriate medication.

10. The method as claimed in claim 8, wherein an appropriate medication section of the recording medium includes a blister style encasement of the appropriate amount of appropriate medication.

11. The method as claimed in claim 8, wherein an medication appropriate section of the recording medium includes a digestible blister style encasement of the appropriate amount of appropriate medication.

12. The method as claimed in claim 8, wherein each medication section is printed with medication identification information.

13. The method as claimed in claim 1, further comprising:
    binding the recording medium in a booklet.

14. The method as claimed in claim 13, wherein the booklet represents a pre-determined period of time.

* * * * *